US006550482B1

(12) United States Patent
Burbank et al.

(10) Patent No.: US 6,550,482 B1
(45) Date of Patent: Apr. 22, 2003

(54) METHODS FOR NON-PERMANENT OCCLUSION OF A UTERINE ARTERY

(75) Inventors: Fred Burbank, San Juan Capistrano; Greig E. Altieri, Laguna Beach; Michael L. Jones, Capistrano Beach, all of CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 0 days.

(21) Appl. No.: 09/556,934

(22) Filed: Apr. 21, 2000

(51) Int. Cl.⁷ .............................................. A61B 19/00
(52) U.S. Cl. ....................................................... 128/898
(58) Field of Search ........................... 128/898; 606/157, 606/158

(56) References Cited

U.S. PATENT DOCUMENTS

| | | | |
|---|---|---|---|
| 4,292,960 A | 10/1981 | Paglione | |
| 4,428,379 A | 1/1984 | Robbins et al. | |
| 4,509,528 A | 4/1985 | Sahota | |
| 4,650,466 A | 3/1987 | Luther | |
| 4,757,823 A | 7/1988 | Hofmeister et al. | |
| 4,994,069 A | 2/1991 | Ritchart et al. | |
| 5,081,997 A | 1/1992 | Bosley, Jr. et al. | |
| 5,108,408 A | * 4/1992 | Lally ........................... | 606/119 |
| 5,201,314 A | 4/1993 | Bosley et al. | |
| 5,226,911 A | 7/1993 | Chee et al. | |
| 5,275,166 A | 1/1994 | Vaitenkunas et al. | |
| 5,289,831 A | 3/1994 | Bosley | |
| 5,383,922 A | 1/1995 | Zipes et al. | |
| 5,456,693 A | * 10/1995 | Conston et al. .............. | 606/192 |
| 5,458,596 A | 10/1995 | Lax et al. | |
| 5,488,958 A | 2/1996 | Topel et al. | |
| 5,507,744 A | 4/1996 | Tay et al. | |
| 5,542,944 A | 8/1996 | Bhatta | |
| 5,549,624 A | 8/1996 | Mirigian et al. | |
| 5,549,824 A | 8/1996 | Trumpf et al. | |
| 5,556,396 A | 9/1996 | Cohen et al. | |
| 5,588,960 A | 12/1996 | Edwards et al. | |
| 5,614,204 A | * 3/1997 | Cochrum ..................... | 424/423 |
| 5,662,680 A | 9/1997 | Desai | |
| 5,672,153 A | 9/1997 | Lax et al. | |
| 5,691,314 A | 11/1997 | Hodgen | |

(List continued on next page.)

FOREIGN PATENT DOCUMENTS

| | | |
|---|---|---|
| DE | 195 28 440 A | 2/1997 |
| EP | 0 472 368 | 2/1992 |
| EP | 0 598 579 | 5/1994 |
| EP | 1 072 282 | 1/2001 |
| GB | 2 311 468 A | 1/1997 |
| WO | WO 95/02370 | 1/1995 |
| WO | WO 95/02371 | 1/1995 |
| WO | WO 98/19713 | 5/1998 |

OTHER PUBLICATIONS

Ravina et al., *Arterial Embolization to Treat Uterine Myomata*, Lancet, Sep. 9, 1995; vol. 346, pp. 671–672.
Hay, D.L., et al., *Hemostasis in Blood Vessels After Ligation*, Am. J. Obstet. Gynecol., Mar. 1989, 160:3, pp. 737–739.

(List continued on next page.)

*Primary Examiner*—Corrine McDermott
*Assistant Examiner*—Thomas Barrett
(74) *Attorney, Agent, or Firm*—Coudert Brothers LLP

(57) ABSTRACT

Non-permanent occlusion of the uterine arteries is sufficient to cause the demise of uterine myomata without unnecessarily exposing other tissues and anatomical structures to hypoxia attendant to prior permanent occlusion techniques. A therapeutically effective transient time of occlusion of a uterine artery to treat uterine fibroid tumors is from 1 hours to 24 hours, and preferably is at least about 4 hours. A therapeutically effective temporary time of occlusion of a uterine artery to treat uterine fibroid tumors is from 1 day (24 hours) to 7 days (168 hours), and preferably is about 4 days (96 hours).

11 Claims, 1 Drawing Sheet

U.S. PATENT DOCUMENTS

| | | | |
|---|---|---|---|
| 5,697,942 | A | 12/1997 | Palti |
| 5,713,896 | A | 2/1998 | Nardelia |
| 5,713,942 | A | 2/1998 | Stern et al. |
| 5,715,832 | A | 2/1998 | Koblish et al. |
| 5,716,389 | A | 2/1998 | Walinsky et al. |
| 5,720,743 | A | 2/1998 | Bischof et al. |
| 5,759,154 | A | 6/1998 | Hoyns |
| 5,766,135 | A | 6/1998 | Terwilliger |
| 5,776,129 | A | 7/1998 | Mersch |
| 5,797,397 | A | 8/1998 | Rosenberg |
| 5,800,378 | A | 9/1998 | Edwards et al. |
| 5,817,022 | A | 10/1998 | Vesely |
| 5,836,906 | A | 11/1998 | Edwards |
| 5,840,033 | A | 11/1998 | Takeuchi |
| 5,895,386 | A | 4/1999 | Odell et al. |
| 5,899,861 | A | 5/1999 | Friemel et al. |
| 5,910,484 | A | 6/1999 | Haupert, Jr. |
| 5,911,691 | A | 6/1999 | Mochizuki et al. |
| 5,921,933 | A | 7/1999 | Sarkis et al. |
| 5,941,889 | A | 8/1999 | Cermak |
| 5,979,453 | A | 11/1999 | Savage et al. |
| 6,015,541 | A | 1/2000 | Greff et al. |
| 6,032,673 | A | 3/2000 | Savage et al. |
| 6,033,398 | A | 3/2000 | Farley et al. |
| 6,034,477 | A | 3/2000 | Peeters et al. |
| 6,035,238 | A | 3/2000 | Ingle et al. |
| 6,045,508 | A | 4/2000 | Hossack et al. |
| 6,066,139 | A | 5/2000 | Ryan et al. |
| 6,077,257 | A | 6/2000 | Edwards et al. |
| 6,106,473 | A | 8/2000 | Violante et al. |
| 6,231,515 | B1 | 5/2001 | Moore et al. |
| 6,254,601 | B1 * | 7/2001 | Burbank et al. ............ 128/898 |
| 6,280,441 | B1 | 8/2001 | Ryan |

OTHER PUBLICATIONS

Brohim, R.M., et al., Development of Independent Vessel Security After Ligation With Absorbable Sutures or Clips, Am. J. Surg., Mar. 1993, vol. 165, pp. 345–349.

Schaefer, C.J., et al., *Absorbable Ligating Clips*, Surg. Gynecol. Obstet., 1982, 154:513–6.

Barth, K., et al., "Long Term Follow–up of Transcatheter Embolization with Autologous Clot, Oxycel and Gelfoam in Domestic Swince", Investigative Radiology, May–Jun. 1977, vol. 12, No. 2, pp. 277–278.

Bateman, W., "Treatment of Intractable Menorrhagia by Bilateral Uterine Vessel Interruption", *American Journal of Obstetrics & Gynecology*, Jul. 15, 1994, vol. 89, No. 6, pp. 825–827.

Brigato, G., et al., Tecnica strumentale non invasive nelle emorragie irrefrenabili del post–partum ("A Noninvasive Instrumental Method in Severe Postpartum Hemorrhages"), Minerva Ginecologica, 1998, vol. 50, No. 7–8, pp. 337–339. (translation attached).

Burbank, Fred, et al., Uterine Artery Occlusion by Embolization or Surgery for the Treatment of Fibroids: A Unifying Hypothesis–Transient Uterine Ischemia, The Journal of the American Association of Gynecologic Laparoscopists, Nov. 2000, vol. 7, No. 4 Supplement, pp. S3–S49. (previously provided to Examiner Corrine McDermott during personal interview on Nov. 28, 2001).

Burbank, Fred et al., "Uterine Artery Occlusion by Embolization or Surgery for the Treatment of Fibroids: A Unifying Hypothesis–Transient Uterine Ischemia", *The Journal of the American Association of Gynecologic Laparoscopists*, Nov. 2000, vol. 7, No. 7 Supplemental, pp. S3–S49.

Fuchs, Karl, "Afibrinogenemia Treated by Ligation of Uterine Arteries", *Gynacologic* 148:407–411 (1959).

Garza Leal, J. et al., "Myoma Treatment by Transient Uterine Ischemia", *The Journal of the American Association of Gynecologic Laparoscopists* 7(3):S31 (Aug. 2000).

Hunerbein, M. et al., "Endoscopic Ultrasound–Guided Real Time Biopsy of Peri–Intestinal Tumors", *Surgical Technology International VII*, 1998, pp. 91–95.

O'Leary, James A., M.D., "Uterine Artery Ligation in the Control of Postcesarean Hemorrage", *The Journal of Reproductive Medicine, Inc.*, 40(3):189–193 (Mar. 1995).

O'Leary, James L., M.D. et al., "Uterine artery ligation in the control of intractable postpartum hemmorage", AM. J. Obst. & Gynec. 94(7):920–924 (Apr. 1, 1966).

"Mick 200–TP Applicator Package", Mick Radio–Nuclear Instruments, Inc., advertisement.

"Multiplanar Biopsy Transverse Scan", Bruel & Kjaer Medical Systems, Inc., advertisement.

"Seeding Device –Proscan Urologic Ultrasound Imaging System", Teknar, advertisement.

Sonopsy Ultrasound Guided Breast Biopsy, NeoVision, advertisement.

"Transrectal Biopsy of the Prostate Gland", Bruel & Kjaer Medical Systems, Inc., advertisement.

* cited by examiner

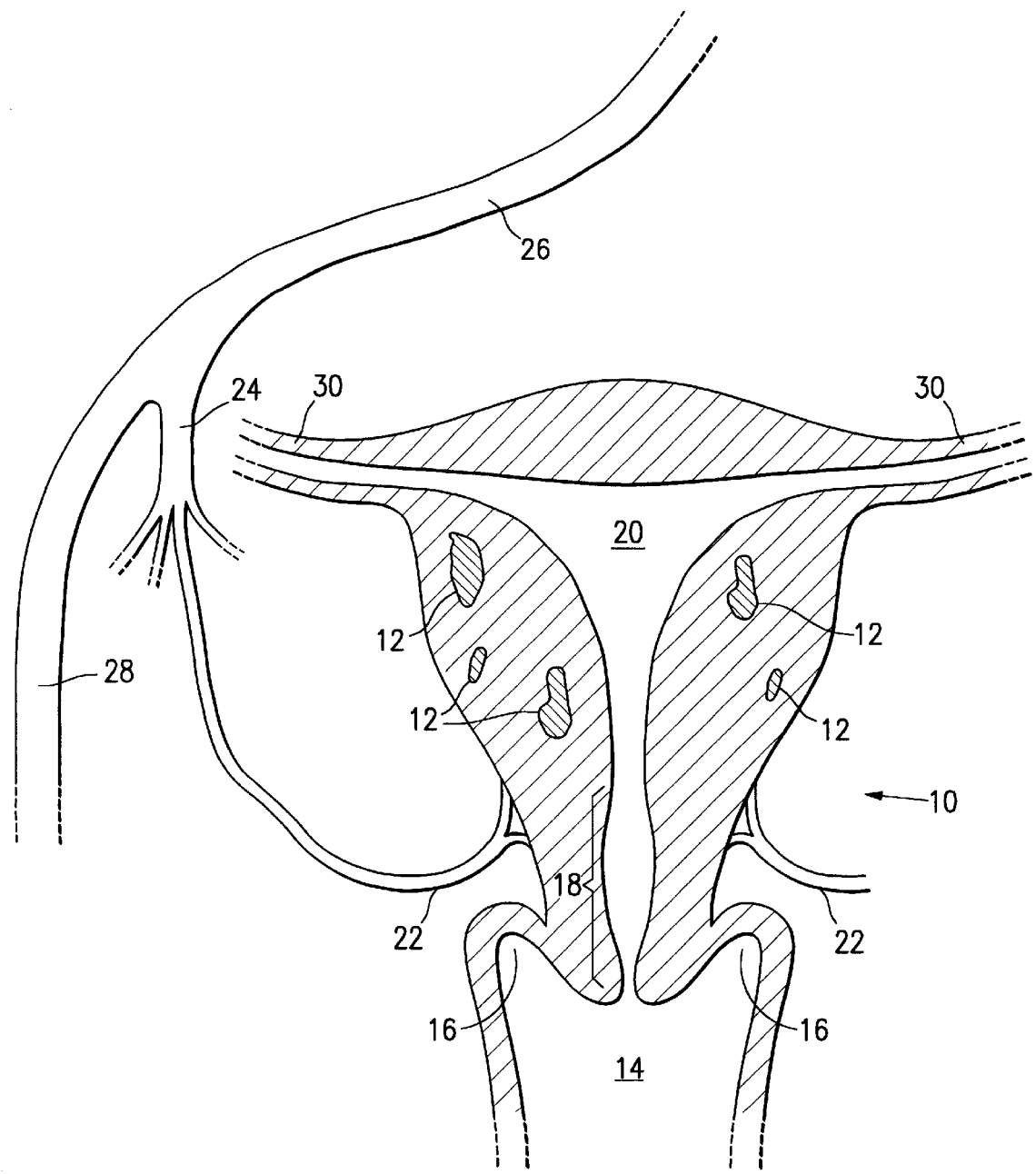

METHODS FOR NON-PERMANENT OCCLUSION OF A UTERINE ARTERY

BACKGROUND OF THE INVENTION

1. Field of the Invention

The present invention relates generally to the treatment of disorders which receive blood flow from the uterine arteries, and more particularly to methods for the non-permanent occlusion of the uterine artery or arteries, specifically for use in treating uterine myomata (fibroids).

2. Brief Description of the Related Art

Hysterectomy (surgical removal of the uterus) is performed on approximately 600,000 women annually in the United States. For approximately 340,000 women, hysterectomy is probably the best current therapeutic choice for the treatment of their diseases (uterine cancer, endometriosis, menorrhagia, and prolapse). For approximately 60,000 women with dysfunctional uterine bleeding (abnormal menstrual bleeding that has no discrete anatomic explanation such as a tumor or growth), newer endometrial ablation techniques may be an alternative to hysterectomy. For approximately 200,000 women with benign but symptomatic (excessive bleeding, pain, and "bulk" sensations) muscular tumors of the uterus, known as leiomyoma or fibroids, newer treatment methods have been developed which may spare these women a hysterectomy, as well.

Hysterectomy for treating uterine fibroid disorders, though effective, has many undesirable characteristics. Thus, any method which can approximate the therapeutic result of a hysterectomy without removing the uterus (and commonly the ovaries since they are closely adjacent to the uterus) would be a significant improvement in this field.

The undesirable characteristics of hysterectomy include a known mortality rate of 0.5 deaths per 1000 hysterectomies. Stated another way, the risk of death within 30 days of hysterectomy is thirty times greater for women who have had a hysterectomy than for women of similar ages and backgrounds who have not had a hysterectomy. Morbidity (medical symptoms and problems short of death) associated with hysterectomy include possible injury to adjacent organs (the bladder, the ureters, and bowel), hospital stay of approximately one week, five to six weeks of slow recovery to normal activity, three weeks of absence from work, direct medical expenses of at least $10,000, indirect cost of time away from work, a future three-fold increase in the incidence of cardiovascular disease, decreased sexual pleasure in approximately thirty percent of women, and depression and anxiety for many years after the hysterectomy for approximately eight percent of women.

Surgically removing fibroids or in situ ablation of uterine fibroids is a bit like eradicating ants in the pantry—they are not all seen from one perspective and there may be a lot of them. Commonly, a diagnosis of uterine fibroids involves the presence of multiple fibroids, often averaging ten fibroids or more per afflicted uterus. Consequently, it is difficult to know which fibroid is causing symptoms to the patient (bleeding, pain, and bulk effects on adjacent organs). Furthermore, fibroids occur at different layers in the uterus. Uterine fibroids can occur adjacent to the lining of the uterus (submucosal fibroid), in the myometrium (intramural fibroid), or adjacent to the outer layer of the uterus (subserosal fibroid). Consequently, if one is directly observing the uterus from the peritoneal cavity, only subserosal fibroids would be seen. If one is directly observing the uterus from the endometrial surface of the uterus, only the submucosal would be seen. Fibroids deep within the wall of the uterus are poorly visualized from either surface. Finally, since fibroids come in all sizes, only the larger fibroids will be seen in any case.

Clearly, the strategy of identifying which individual fibroid is causing symptoms (when there are often many), finding that fibroid, and then either removing or destroying that individual fibroid is a rather complex strategy. It is therefore easy to understand why the hysterectomy is such a common surgical choice. With hysterectomy, all uterine fibroids are removed in one stroke.

In 1995, it was demonstrated that fibroids, in a uterus that contained one or multiple fibroids, could be treated without hysterectomy using a non-surgical therapy, specifically comprising bilateral intraluminal occlusion of the uterine arteries (Ravina et al., "Arterial Embolization to Treat Uterine Myomata", Lancet Sep. 9, 1995; Vol. 346; pp. 671–672, incorporated by reference in its entirety herein). This technique is known as "uterine artery embolization". The technique uses standard interventional radiology angiographic techniques and equipment, whereby the uterine arteries are accessed via a transvascular route from a common femoral artery into the left and right uterine arteries.

Three facts explain the success of uterine artery embolization. First, it has been established that pelvic bleeding from a wide variety of sources (e.g., auto accidents, surgical errors, and post partum hemorrhage) can be effectively controlled with embolization techniques using coils placed in arterial and venous lumens (U.S. Pat. Nos. 4,994,069, 5,226,911, and 5,549,824, all of which are incorporated in their entireties herein) (available from Target Therapeutics), or particles (GELFOAM pledgets, available from Upjohn, Kalamazoo, Mich., or IVALON particles, available from Boston Scientific).

Second, fibroids live a tenuous vascular life with very little ability to recruit a new blood supply from the host when the primary blood supply is compromised. Third, the uterus has a dual (or redundant) blood supply; the primary blood supply is from the bilateral uterine arteries, the secondary blood supply from the bilateral ovarian arteries.

Consequently, when both uterine arteries are occluded, i.e. bilateral vessel occlusion, the uterus and the fibroids contained within the uterus are both deprived of their blood supply. However, as demonstrated by Ravina et al., the effect on the fibroid is greater than the effect on the uterus. In most instances, the fibroid withers and ceases to cause clinical symptoms.

The uterine artery embolization technique utilized by Ravina et al. uses standard transvascular equipment, available in typical interventional radiology angiography suite. This equipment includes guide catheters to selectively enter the tortuous right and left uterine arteries, Ivalon or Gelfoam particles, and intravascular coils. With skill and these standard angiographic tools, the uterine arteries can be occluded bilaterally and fibroid disease treated through a 2 mm hole in the right groin and through the right common femoral artery. Following the procedure, the arterial puncture site is held with manual pressure for fifteen minutes. While post-procedural pain is often significant, and requires intravenously delivered pain medication, the patient is typically fully recovered in a number of days.

The problem with uterine artery embolization is simple. The physicians who know how to do the procedure are interventional radiologists, who do not take care of gynecology problems. The physicians who take care of gynecology problems do not possess the skill necessary to perform catheter based uterine artery embolization. Accordingly, only thousands of uterine artery embolizations have been performed, worldwide, over the past three years, whereas hundreds of thousands of hysterectomies have been performed each year for uterine fibroids which are symptomatic.

Currently, many physicians continue to embolize the uterine artery with PVA particles. As reported by the Society for Cardiovascular and Interventional Radiology in late 1999, some 6000 cases have been performed within the United States. Currently the annualized run rate for this procedure is approximately 4500 cases per year.

Previously, physicians have permanently, surgically ligated the uterine artery utilizing metal vascular clips. This procedure has been performed laparoscopically and requires a great deal of surgical skill to access, identify, dissect, and ligate the uterine arteries. This requirement for high skill and a full surgical approach has limited the use of surgical ligation of the uterine arteries as a clinical alternative for uterine fibroid treatment.

The current treatments offered to women focus on permanent or near permanent occlusion methods for the uterine artery. These methods include (the expected longevity of the embolic agent is given parenthetically): embolizing with PVA particles (6 months to permanent in situ); embolizing with stainless steel coils (permanent in situ); embolizing with Gelfoam (3 to 4 weeks before degradation of the embolic particles); surgical ligation with metal vascular clips (permanent); and surgical ligation with RF ablation (permanent).

All of the prior art devices and methods are therefore aimed at permanent occlusion of the uterine artery, resulting in redirection of the blood flow to the uterus through collateral circulation. The patients which suffer most dramatically from uterine myomata are women of child bearing age who may desire to bear additional children. The current methods of embolizing or ligating uterine arteries are specifically contraindicated for women who desire to bear additional children. This is the realization of inadequate blood supply to the uterus because of the loss of the uterine arteries, the primary blood supply. A few reports have been cited of women who have undergone uterine artery embolization with PVA particles and then gone on to become pregnant and deliver normal babies. Reports have also been cited of women who have experienced premature menopause due to ovarian failure from these same procedures.

While it is apparent that uterine artery embolization with the current embolic agents or ligation techniques is effective for treating uterine myomata, it is also apparent from a review of case reports and complications that this treatment is in need of a substantial improvement in safety.

There therefore still remains a need in the art for improvements in methods, processes, and techniques for occluding the uterine arteries.

SUMMARY OF THE INVENTION

According to a first exemplary embodiment, a process of treating a condition of a patient comprises the steps of temporarily occluding a uterine artery for a therapeutically effective time period, and reestablishing blood flow through the uterine artery at the termination of said therapeutically effective time period.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which:

the drawing FIGURE illustrates portions of a uterus and some adjacent anatomical structures.

DESCRIPTION OF THE PREFERRED EMBODIMENTS

Non-permanent occlusion of the uterine artery is sufficient to cause the demise of uterine myomata without unnecessarily exposing other tissues and anatomical structures to hypoxia attendant to prior permanent occlusion techniques. In the context of the present invention, a therapeutically effective transient time of occlusion of a uterine artery to treat uterine fibroid tumors is from 1 hour to 1 day (24 hours). Also in the context of the present invention, a therapeutically effective temporary time of occlusion of a uterine artery to treat uterine fibroid tumors is from 1 day (24 hours) to 7 days (168 hours), and preferably is about 3–4 days (72–96 hours).

Methods for non-permanent uterine artery occlusion in accordance with the present invention allow for substantial improvements in safety and efficacy of this procedure over prior techniques. Processes in accordance with the present invention preferably result in death to the entire uterine fibroid cell line, a normal blood supply to the uterus within a short period of time after reestablishment of the blood supply through the uterine artery or arteries, preferably about a week, and no fear of premature menopause and ovarian failure due to particulate embolization of the ovarian artery or ovaries.

Methods for non-permanent uterine artery occlusion of the present invention are all aimed at producing the following events, preferably in the sequence indicated. Blood flow in the uterine artery is slowed or stopped by occluding or embolizing the artery. This stoppage of blood flow creates a clotting cascade within the artery in a fashion well known to those skilled in the art. Once blood flow has ceased and the vessel is filled with blood clots or thrombus, uterine fibroids, and more particularly the cells of the uterine fibroids, suffer a nearly immediate death because of the cessation of blood flow to them. The uterus becomes anoxic, but is partially supplied by the ovarian arteries and other collateral circulation. This collateral circulation is adequate to keep the uterine tissues alive and allow for it to recover as the total blood flow to the uterus returns to normal.

The thrombus formed within the transiently or temporarily occluded blood vessel is addressed by the blood system with a series of enzymes which attempt to lyse the thrombus. This cycle is predicable and effective, and it can be assisted with various thrombolytic agents such as tissue plasminogen activator (tPA). In order to assure that the thrombus is well formed to occlude the uterine artery in accordance with the processes of the present invention, hemostasis should be maintained for at least about 1 hour to about 24 hours. Therefore, it is preferable that the mechanism which initiates formation of the thrombus, described in greater detail below, stays in place at least 1 hour to 24 hours to provide for the death of the fibroid cell line. After this initial period to initiate and maintain the formation of a thrombus in the artery, preferably about 1–24 hours, the mechanism can be removed. As described in greater detail below, the mechanism for occluding the uterine artery can take any one of a number of forms in accordance with the present invention, and therefore can be removed by a number of ways, including resorption in the body, disintegration of the mechanism, and physical removal from the artery. As will be readily appreciated by one of ordinary skill in the art, the present invention is not limited to the specific examples herein of mechanisms which are useful for occluding a uterine artery, and other suitable methods and devices are also within the spirit and scope of the present invention.

Steps of methods in accordance with the present invention will now be described with reference to particular mechanisms which occlude one or both uterine arteries in order to initiate the clotting cascade which results in thrombus formation. While it is likely sufficient that the use of only one of the following modalities will result in the occlusion of a uterine artery, it is also within the scope of the present invention to Simultaneously or serially employ multiple modalities to occlude a single uterine artery.

The following are merely provided by way of example and not of limitation. Access to the uterine arteries can be had by any of a number of procedures, including, but not limited to: laparoscopic access; transvaginal access through the vaginal wall; access as described in copending U.S. patent application Ser. No. 09/207,572, entitled "Devices And Method For Occlusion of The Uterine Arteries", invented by Burbank et al., the entire contents of which are incorporated herein by reference; and/or transluminal access, as described by Ravina et al, above.

One or both of the uterine arteries of the patient are occluded using one of the devices and associated procedures described below. The adequacy of the occlusion can then optionally be measured by any process suitable for the measurement of blood flow, e.g., doppler ultrasound. The time of initial occlusion can then optionally be marked so that the total time of occlusion of the artery can be ascertained. Although it is preferable that both of the patient's uterine arteries are occluded for the minimum time periods necessary to initiate thrombus formation, and more preferable that the occlusion times for both arteries overlap by at least this minimum time, it is also within the scope of the present invention to occlude the uterine arteries serially.

Turning now to the drawing figures, the drawing FIGURE illustrates portions of a uterus of a patient and some of her adjacent anatomical structures, reference to which can be made for a better understanding of the present invention. The drawing FIGURE illustrates a uterus 10 which is afflicted with one or more fibroid tumors 12. The patient's vagina 14 includes the vaginal fornix 16. The cervix 18 extends between the uterine cavity 20 and the vagina 14. As discussed further herein, the uterine arteries 22 extend to the uterus 10 and supply the uterus (and the fibroids) with oxygenated blood. While one of ordinary skill in the art will appreciate that uterine arteries' internal diameters will normally vary within groups of patients, and therefore that the present invention relates to non-permanent occlusion of uterine arteries of various sizes, typically uterine arteries have internal diameters of about 2 mm to about 4 mm prior to (upstream of) the first order branches of the artery at the uterus. The first order branches, typically, have internal diameters of less than 2 mm, with higher order branches having again smaller internal diameters. Therefore, while the processes in accordance with the present invention can be performed on a uterine artery prior to the first order branches, the present invention also can be performed on higher order branches with smaller internal blood clots. Thus, while the following descriptions reference the uterine artery, the term uterine artery also includes higher order branches of the uterine artery and the non-permanent occlusion of them.

As illustrated in the drawing FIGURE, the uterine arteries 22 extend generally laterally from the outer portions of the uterus in positions close to the vaginal fornix 16. The uterine arteries 22 are themselves supplied with blood from the internal iliac artery 24, which branches from the common iliac artery 26 with the external iliac artery 28. Although not illustrated in the drawing FIGURE, the external iliac artery 28 leads to the common femoral artery, through which endovascular access to the uterine arteries 22 can be made in accordance with the present invention. As one of ordinary skill in the art is well-acquainted with techniques of transluminal, endovascular access through a femoral artery of a patient to the vasculature of a patient, a familiarity therewith will be presumed herein and details will not be further provided. Fallopian tubes 30 extend away from the uterus 10.

It has been observed and reported that blood vessel hemostasis of greater than 4 days (96 hours) is necessary to permanently occlude a blood vessel. See Hay, D. L., et al., "Hemostasis in blood vessels after ligation", Am. J. Obstet. Gynecol. 160:3, pp. 737–739 (March 1989), and Brohim, R. M., et al., "Development of independent vessel security after ligation with absorbable sutures or clips", Am. J. Surg., Vol. 165, pp. 345–349 (March 1993), the entire contents of both of which are incorporated by reference in their entireties herein by reference. Thus, as the processes in accordance with the present invention are directed to non-permanent, transient and/or temporary occlusion of the uterine arteries, it is necessary to remove the vessel occlusion at a time prior to the artery closing permanently and after a therapeutically effective time period of hemostasis for the uterine fibroid cell line to have died from the lack of a sufficient blood supply.

Throughout the following examples, reference is made to resorbable materials out of which devices useful in the present invention can be made. Exemplary resorbable materials include, but are not limited to: polyglycolic acid, including low-molecular weight polyglycolic acid; polyglycolic acid/polyethylene glycol hydrogel; copolymers of lactide and glycolide; polyvinyl alcohol; polyvinylpyrrolidone; gelatin; crosslinked hyaluronic acid; combinations or mixtures of one or more of the foregoing materials; as well as other resorbable materials, which are also usable and within the scope of the present invention as will be readily apparent to one of ordinary skill in the art.

Transient Occlusion

After at least 1 hour of occlusion, preferably 1–24 hours, more preferably 4–24 hours, of total occlusion time for a uterine artery, the device, mechanism, or modality by which the artery was occluded is removed, permitting reestablishment of the blood flow through the uterine artery to the uterus. A therapeutically effective transient time of occlusion of a uterine artery to treat uterine fibroid tumors is from 1 hour to 1 day (24 hours). By occluding a uterine artery for a therapeutically effective transient time of occlusion, the blood flow through the uterine artery is slowed sufficiently, and preferably stopped, for a time sufficient for a blood clot to form in the vessels of the uterus and fibroids growing on the uterus. Once the blood clot is formed, the clot itself can assume the task of slowing or stopping blood flow through the uterine artery, and the device, mechanism, or modality which initially slowed or stopped blood flow (described in greater detail below) can be removed. As will be readily appreciated by one of ordinary skill in the art, the clot will then begin to be broken down or lysed by the body. This lysing process can optionally be assisted by a systemic or localized administration of a thrombolytic agent, such as tPA, or the like, if the practitioner elects to do so.

(1) Transient embolic particle: a swellable and expandable, position controllable embolic particle can be used in the transient processes of the present invention. Preferably, the material is selectively placed within the uterine artery angiographically, directly injected into the uterine artery through the vessel wall, or by other processes readily apparent to one of ordinary skill in the art, such as under ultrasound or MRI guidance. The material is resorbable or disintegratable in vivo in at least about 1 hour up to about 1 day (24 hours). Materials for such a particle preferably are a 75 to 300 bloom gelatin, or a copolymer of polyglycolic acid and polyethylene glycol which swell when placed in the bloodstream to form an occlusion in the artery. Other materials for such an embolic agent include, but are not limited to, a crosslinked hyaluronic acid or other biodegradable biocompatible polymer.

(2) Autologous clot: an autologous blood clot can be formed in the uterine artery, which slows or stops blood flow through the uterine artery for a therapeutically effective transient time period. As well appreciated by one of ordinary skill in the art, an autologous clot can be formed by withdrawing a volume of blood from the patient, allowing it to clot by itself, optionally drying and finely dividing the dried clot mass (e.g., in a blender), and reinjecting the clotted blood (or dried sample) back into the uterine artery. The injection can be directly through the vessel wall or transluminally through a catheter, such as an appropriately-sized angiography catheter. The reinjected material initiates the clotting sequence in the uterine artery and forms a clot which slows or stops blood flow. One benefit from the use of an autologous clot to embolize the uterine artery is that, as the blood was originally drawn from the patient herself, the material injected into her uterine artery will naturally lyse and there will be no concern about the ability of the body to absorb or degrade the injected material. Furthermore, the injection of a sample as described above does not require compression of the uterine artery, because the clotting sequence initiates rapidly, and therefore there is minimal damage to the artery itself.

(3) Temporary balloon occlusion: balloon catheters are well known to those of skill in the art, and therefore a familiarity therewith will be assumed. A balloon catheter with a fully inflated diameter sufficient to slow or stop the flow of blood for a therapeutically effective transient time period is advanced through the vasculature to the uterine artery, and the balloon is inflated for a time sufficient for a blood clot to form. A suitable pathway for advancing such a balloon catheter is described in Revina, supra. For example, the balloon can be inflated for between about 15 minutes and about 20 minutes. After this time period, the balloon is deflated, the catheter is removed, and the blood clot begins to be degraded by the natural lysing processes. Both detachable balloons, with which one of ordinary skill in the art is well acquainted, and balloons fixed to catheters can be used. Further optionally, detachable or fixed balloons in accordance with the present invention can be formed of a resorbable material and inflated with a biocompatible fluid. Such resorbable balloons do not require deflation, although they can be deflated if the practitioner elects to do so, because the balloon material will be resorbed into the patient's body within a predetermined time. According to preferred embodiments, balloon occlusion is performed with a detachable balloon which is formed of a resorbable material.

(4) Selective vasospasm: Blood vessels have demonstrated a vessel spasm reaction to certain substances, including dimethyl sulfoxide (DMSO), ethyl alcohol, irrigation water, and other non-physiological fluids, when the substance is present in sufficient concentration in the blood vessel. These vessel spasms can be so severe that the vessel is completely closed down, or self-constricted, and some spasms cannot be alleviated by the use of anti-spasm drugs, such as papaverine hyrdochloride. This spasm reaction can, in accordance with the present invention, be used to slow or stop the flow of blood through a uterine artery for a time sufficient for a blood clot to form. Thus, any substance which will cause such a vessel spasm reaction, including those listed above, can be injected into the vessel to cause a spasm and closure of the vessel. The injection can be directly through the vessel wall or transluminally through a catheter, such as an appropriately-sized angiography catheter.

(5) Intra-arterial injection of hemostatic agent: Bovine thrombin has been used as a topical hemostatic agent to stop bleeding due to trauma or surgical resection of vascular organs. In accordance with the present invention, a hemostatic agent can be injected into the uterine artery to initiate a clotting cascade, which can be nearly instantaneous. The injection can be directly through the vessel wall or transluminally through a catheter, such as an appropriately-sized angiography catheter. Suitable hemostatic agents include, but are not limited to: thrombin, including human and bovine thrombin; fibrinogen; thromboplastin, vasopressin, algin, alginic acid, and combinations or mixtures thereof.

Temporary Occlusion

After at least 1 day (24 hours), preferably 1–7 days, more preferably 3–4 days, of total occlusion time for a uterine artery, the device, mechanism, or modality by which the artery was occluded is removed, permitting reestablishment of the blood flow through the uterine artery to the uterus. Different from transient occlusion discussed above, temporary occlusion does not rely solely on the blood clot formed as a result of the slowing or stoppage of blood flow through the uterine artery. In accordance with the present invention, temporary occlusion benefits from the combination of both the device, mechanism, or modality and the blood clot to limit or stop blood flow through the uterine artery.

(1) Suture applier: Suture appliers utilizing short duration suture can be used to ligate the uterine artery or arteries. A suture applier housing a short lived bioresorbable suture filament, such as a low-molecular weight polyglycolic acid or polyglycolic acid/polyethylene glycol hydrogel filament can be used, for example. Because the prior procedures which are currently used endeavor to permanently occlude arteries, current suture materials such as Vicryl, Maxon, gut, or other resorbable suture filaments which have a relatively long duration in vivo, e.g., at least 10 days, are not usable in the present invention in their commercially available form. Typical suture materials are designed to retain their strength for sufficient time to allow for tissue to heal together and strengthen before the suture material is resorbed. In the context of the present invention and as shown by Hay and Brohim, this would mean permanent occlusion of the uterine artery.

The only commercially available material which has an absorption time which approaches the time period required by the present invention is Vicryl Rapide (Johnson & Johnson), a copolymer of lactide and glycolide, with a reported lifetime of 7 to 10 days in vivo. In order to use this product in the present invention as an absorbable suture, it is necessary to shorten this absorption time to between 1–7 days, preferably 3–4 days. While other examples of ways to modify the absorption time of this product are within the scope of the present invention, examples include changing the ratio of the constituent polymers in the copolymer and "pre-aging" the commercially available version, such as by gamma-irradiation, exposing the product to a suitable solvent for a period of time, or the like.

In order to use suture materials to ligate and occlude a uterine artery in accordance with the present invention, a length of suture material with an in vivo lifespan before absorption of between 1–7 days, preferably 3–4 days, is looped around the uterine artery of interest and tied to collapse the vessel upon itself and stop the blood flow therethrough.

In less preferred embodiments of the present invention, a non-absorbable suture can be used to ligate and collapse the uterine artery for a therapeutically effective time period in accordance with the present invention, and thereafter the suture is removed in a known manner.

(2) Resorbable vascular clip: a vascular clip designed to snap or plastically deform around the uterine artery can be used in the processes of the present invention, formed of a resorbable material as described above. The use of resorbable vascular clips has been reported by Brohim et al, supra, and Schaefer, C. J., et al., "Absorbable ligating clips", Surg. Gynecol. Obstet., 154:513–6 (1982), and has been commercially available as Poly Surgiclip (U.S. Surgical Corp., Norwalk, Conn.), and Absolok™ Extra (Ethicon Endo-Surgery, Inc.). As an example, a vascular clip usable in the present invention can be made of a low molecular weight polyglycolic acid (e.g., 6000 to 7000 Daltons) which would quickly degrade in vivo via hydrolysis. Alternately, a vascular clip can be fabricated of polyglycolic acid having a higher molecular weight, but being sintered or bonded together with a dissolvable material such as polyvinyl alcohol, gelatin, or the like. The dissolvable material of the clip hydrates and goes into solution in vivo, gradually weakening the structure of the clip until it disintegrates, In order to use resorbable clips to occlude a uterine artery in accordance with the present invention, a resorbable clip with an in vivo lifespan before resorption of between 1–7 days, preferably 3–4 days, is secured around the uterine artery of interest in a known manner to collapse the vessel upon itself and stop the blood flow therethrough.

(3) Removable vascular clip: Currently several models of spring clamps or ratchet clamps are made for surgical occlusion of blood vessels during vascular surgeries. One manufacturer of suitable clamps is Applied Medical Resources Inc, Laguna Hills, Calif. While currently available clamps or clips are relatively bulky because they are designed for open vascular surgeries, they can be used in the processes of the present invention. When the present process' therapeutically effective time period is completed, the clamp is removed and blood flow is reestablished within the vessel. Preferably, the clamp is a relatively small clip so that when a surgical incision is made to install it, the incision does not have to be large. The use of smaller clips permits release of the surgical clamp release mechanism without reopening the surgical incision to gain access to the clip. Alternatively, a relatively large clip can be used directly on the vaginal wall to ensnare and occlude the uterine artery which is located on the other side of the wall.

(4) Temporary resorbable embolic particles or materials: a swellable, position controllable embolic particle can be used in the processes of the present invention. Preferably, the material is selectively placed within the uterine artery angiographically, directly injected into the uterine artery through the vessel wall, or by other processes readily apparent to one of ordinary skill in the art, such as under ultrasound or MRI guidance. The material is resorbable or disintegratable in vivo in at least about 1 day up to about 7 days. Materials for such a particle preferably are a 75 to 300 bloom gelatin, or a copolymer of polyglycolic acid and polyethylene glycol which swell when placed in the bloodstream to form an occlusion in the artery. Other materials for such an embolic agent include, but are not limited to, a crosslinked hyaluronic acid or other biodegradable biocompatible polymer.

(5) Thrombus forming energy: a source of energy, e.g., thermal, EM, or the like, can be used in the processes of the present invention. A familiarity with such sources of energy is assumed herein, as such sources are readily commercially available. As will be readily appreciated by one of ordinary skill in the art, energy, such as high intensity focused thermal, ultrasound, electrosurgical energy, or the like initiate the clotting cascade in blood. Thus, in order to use energy to occlude a uterine artery in accordance with the present invention, the energy is applied, preferably in a focused way, on the uterine artery to form a thrombus therein. By adjusting the application of the energy to the blood within the artery, an in vivo lifespan of between 1–7 days, preferably 3–4 days, of a thrombus can be achieved.

(6) Direct gaseous embolus injection: a volume of a gas can be directly injected into the uterine artery, either through a transluminal approach or through the vessel wall. As well appreciated by one of ordinary skill in the art, gas embolisms cause cessation of blood flow through a blood vessel, which in the present invention is used to initiate the clotting sequence. The gas used to embolize the uterine artery is selected to be insoluble in the bloodstream and/or will not diffuse through the uterine artery vessel walls at patient body temperature (approximately 98.6° F., 37.0° C., for human patients), but may also be selected to be partially soluble in blood and/or will partially diffuse through the vessel wall at a rate such that the gas embolism retains sufficient volume to slow or stop blood flow through the uterine artery for a time sufficient for a blot clot to form. Examples of gases which can be used in accordance with the present invention include, but are not limited to, $N_2$, Ar, Kr, $NO_2$, butane, butylene, cyclopropane, propane, and combinations or mixtures thereof. In general, however, gasses suitable for use in the embolization processes in accordance with the present invention have low to no solubility in water or blood, and/or low or no diffusivity through the vessel wall, at the patient's body temperature, and are biocompatible at the total volumes used. Once the therapeutically effective time period of the present invention has expired, the gas embolism is removed or absorbed into the body. While many mechanisms are suitable in the present invention for removing the gas embolism, the gas embolism can be directly aspirated out of the vessel lumen (e.g., by a transluminal approach or directly through the vessel wall) to reinitiate blood flow through the uterine artery.

In addition to the foregoing steps in the processes of the present invention, removal of a blot clot or thrombus can be accelerated by the use of an agent which lyses the clot, including the administration of tPA to the patient after the therapeutically effective time period.

While the invention has been described in detail with reference to preferred embodiments thereof, it will be apparent to one skilled in the art that various changes can be made, and equivalents employed, without departing from the scope of the invention. While specific reference has been made to female adult human patients, processes in accordance with the present invention also include occlusion of one or both of the uterine arteries of any female patient that has uterine arteries, including pediatric humans and other mammals.

What is claimed is:

1. A process of treating a condition of a patient, comprising the steps of:

non-permanently occluding a uterine artery for a therapeutically effective time period; and reestablishing blood flow through the uterine artery at the termination of said therapeutically effective time period;

wherein said step of non-permanently occluding a uterine artery comprises clamping directly on the vaginal wall to ensnare and occlude the uterine artery which is located on the other side of the wall to stop blood flow through said uterine artery.

2. A process in accordance with claim 1, wherein said therapeutically effective time period is between 1 hour and 168 hours.

3. A process in accordance with claim 1, wherein said therapeutically effective time period is between 1 hour and 24 hours, and said step of non-permanently occluding comprises transiently occluding a uterine artery.

4. A process in accordance with claim 1, wherein said therapeutically effective time period is between 24 hours and 168 hours, and said step of non-permanently occluding comprises temporarily occluding a uterine artery.

5. A process in accordance with claim 1, wherein said therapeutically effective time period is between 72 hours and 96 hours, and said step of non-permanently occluding comprises temporarily occluding a uterine artery.

6. A process in accordance with claim 1, wherein said step of clamping comprises clamping with a clamp formed of a resorbable material.

7. A process in accordance with claim 6, wherein said resorbable material comprises polyglycolic acid.

8. A process in accordance with claim 7, wherein said resorbable material further comprises a dissolvable material selected from the group consisting of polyvinyl alcohol and gelatin.

9. A process in accordance with claim 1, wherein said condition comprises the presence of uterine fibroids.

10. A process in accordance with claim 1, wherein said step of non-permanently occluding a uterine artery comprises non-permanently occluding two uterine arteries.

11. A process in accordance with claim 1, wherein said step of clamping comprises clamping with a surgical clamp, and wherein said step of reestablishing blood flow further comprises the step of removing the surgical clamp from the vaginal wall.

* * * * *